US009683267B2

(12) United States Patent
Gasik

(10) Patent No.: US 9,683,267 B2
(45) Date of Patent: Jun. 20, 2017

(54) IN VITRO TEST METHOD FOR IMPLANT MATERIALS

(75) Inventor: Michael Gasik, Helsinki (FI)

(73) Assignee: Aalto University Foundation, Aalto (FI)

(*) Notice: Subject to any disclaimer, the term of this patent is extended or adjusted under 35 U.S.C. 154(b) by 0 days.

(21) Appl. No.: 14/111,740

(22) PCT Filed: Apr. 13, 2012

(86) PCT No.: PCT/FI2012/050362
§ 371 (c)(1),
(2), (4) Date: Oct. 14, 2013

(87) PCT Pub. No.: WO2012/140325
PCT Pub. Date: Oct. 18, 2012

(65) Prior Publication Data
US 2014/0038175 A1 Feb. 6, 2014

Related U.S. Application Data

(60) Provisional application No. 61/475,684, filed on Apr. 15, 2011.

(51) Int. Cl.
C12M 1/34 (2006.01)
C12Q 1/70 (2006.01)
A61F 2/46 (2006.01)
G01N 3/24 (2006.01)
G01N 3/32 (2006.01)
C12Q 1/18 (2006.01)
A61F 2/28 (2006.01)

(52) U.S. Cl.
CPC .............. *C12Q 1/70* (2013.01); *A61F 2/468* (2013.01); *C12M 41/36* (2013.01); *C12M 41/46* (2013.01); *C12Q 1/18* (2013.01); *G01N 3/24* (2013.01); *G01N 3/32* (2013.01); *A61F 2/28* (2013.01); *G01N 2203/0089* (2013.01)

(58) Field of Classification Search
CPC . A61F 2/468; G01N 3/20; G01N 3/22; G01N 3/24; G01N 3/32
USPC .................................................... 435/287.1
See application file for complete search history.

(56) References Cited

U.S. PATENT DOCUMENTS

| 5,217,899 | A | 6/1993 | Shapiro et al. |
| 5,521,087 | A | 5/1996 | Lee et al. |
| 6,107,081 | A * | 8/2000 | Feeback ............... A61B 5/1108 435/284.1 |
| 6,121,042 | A | 9/2000 | Peterson et al. |
| 2002/0116054 | A1 | 8/2002 | Lundell et al. |
| 2003/0125804 | A1 | 7/2003 | Kruse et al. |
| 2004/0016301 | A1 | 1/2004 | Moreno et al. |
| 2004/0219659 | A1 | 11/2004 | Altman et al. |
| 2005/0153436 | A1 | 7/2005 | Vilendrer |
| 2007/0169565 | A1 | 7/2007 | Schulz et al. |
| 2008/0280360 | A1 * | 11/2008 | Kaplan et al. ................ 435/396 |
| 2010/0221698 | A1 | 9/2010 | Wei et al. |
| 2010/0255582 | A1 | 10/2010 | Porter et al. |
| 2010/0262227 | A1 * | 10/2010 | Rangwala et al. ........... 623/1.16 |

FOREIGN PATENT DOCUMENTS

| WO | WO 84/03047 A1 | 8/1984 |
| WO | WO 03/009780 A2 | 2/2003 |
| WO | WO 2007/143688 A2 | 12/2007 |
| WO | WO 2008/022944 A2 | 2/2008 |

OTHER PUBLICATIONS

Mow et al. Basic Orthopaedic Biomechanics and Mechano-Biology; Third Ed. (2005) pp. 622.*
Byung-Soo et al. Tissue Engineering of Smooth Muscle Under a Mechanically Dynamic Condition; Journal of Microbiology and Biotechnology, vol. 13, No. 6 (2003) pp. 841-845.*
Kim et al. Cyclic Mechanical Strain Regulates the Development of Engineered Smooth Muscle Tissue; Nature Biotechnology, vol. 17 (1999) pp. 979-983.*
Thurner et al. High-Speed Photography of Compressed Human Trabecular Bone Correlates Whitening to Microscopic Damage; Engineering Fracture Mechanics, vol. 74 (2007) pp. 1928-1941.*
Červinka, M., et al., "In Vitro Toxicity Testing of Implantation Materials Used in Medicine: Effects on Cell Morphology, Cell Proliferation and DNA Synthesis," Toxicology In Vitro, Jan. 1990, pp. 711-716, vol. 4, No. 4/5, Pergamon Press plc., Great Britain.
Iyer, S. S., et al., "A 'Biorelevant' system to Investigate In Vitro Drug Released from a Naltrexone Implant," International Journal of Pharmaceutics, Mar. 2007, pp. 104-118, vol. 340, Issues 1-2, Elsevier, The Netherlands.
International Searching Authority, International Search Report for International Application No. PCT/FI2012/050362, mailed Sep. 7, 2012, 5 pages, National Board of Patents and Registration of Finland, Finland.
Mow, V.C., et al., "Basic Orthopaedic Biomechanics and Mechano-Biology, 3rd Edition", 2005, relevant pp. 620-622, 624, 626 and 640, Lippincott Williams & Wilkins, USA.
Huiskes, R., et al., "A Biomechanical Regulatory Model for Periprosthetic Fibrous-Tissue Differentitation", Journal of Materials Science, Materials in Medicine, 1997, pp. 785-788, vol. 8, Chapman & Hall, Great Britain.

(Continued)

Primary Examiner — Scott Long
Assistant Examiner — Paul Martin
(74) Attorney, Agent, or Firm — Alston & Bird LLP

(57) ABSTRACT

The invention relates to a method for in vitro testing of specimens, such as biomaterials or implants, wherein the method comprises at least immersing at least a part of the test specimen into a liquid media, controlling the liquid media, controlling surrounding environment, providing a predetermined non-destructive force to the specimen, and measuring reactions of the specimen or constituents of the liquid media. Further it relates to an apparatus for in vitro testing.

11 Claims, 1 Drawing Sheet

(56) References Cited

OTHER PUBLICATIONS

Figure 1:
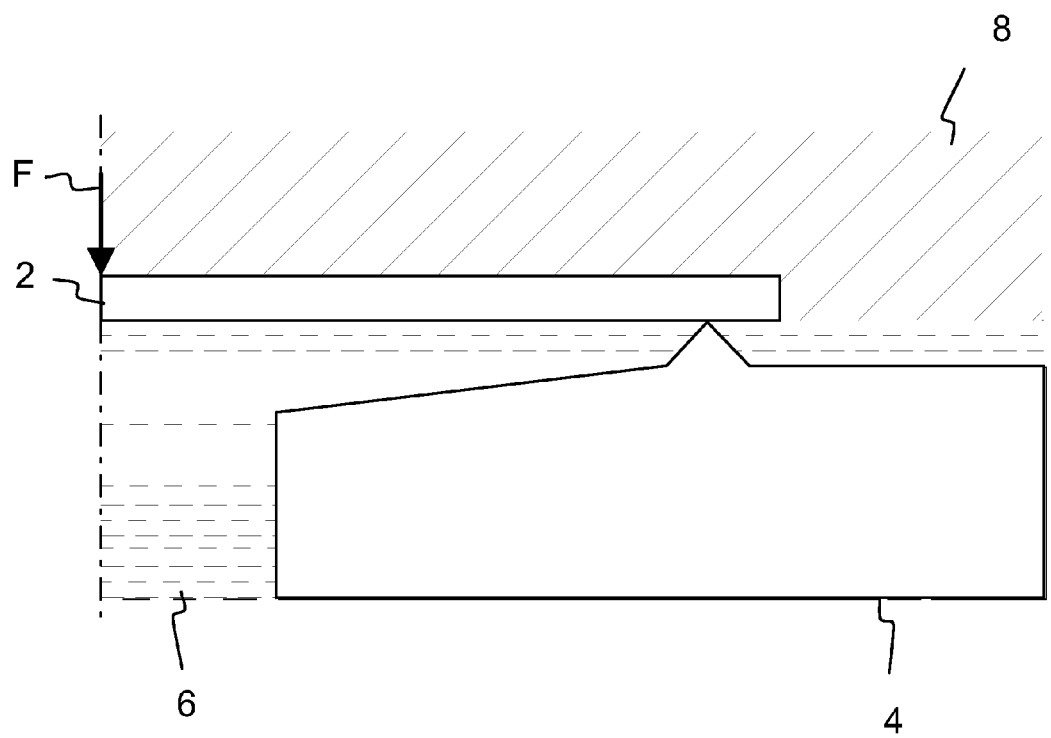

Prendergast, P.J., et al., "Biophysical Stimuli on Cells During Tissue Differentiation at Implant Interfaces", Journal of Biomechanics, 1997, pp. 539-548, vol. 30, No. 6, Elsevier Science Ltd., Great Britain.

Søballe, K., et al.,"Tissue Ingrowth into Titanium and Hydroxyapatite-Coated Implants During Stable and Unstable Mechanical Conditions", Journal of Orthopaedic Research, 1992, pp. 285-299, vol. 10, No. 2, Raven Press, Ltd, USA.

Van Der Meulen, M.C.H., et al., "Why mechanobiology? A Survey Article," Journal of Biomechanics, 2002, pp. 401-414, vol. 35, Elsevier Science Ltd., Great Britain.

European Patent Office, Extended European Search Report for Application No. 12770773.5, Sep. 4, 2014, 8 pages, Germany.

Hertzberg, Richard W., "Deformation and Fracture Mechanics of Engineering Materials", 1976, pp. 440-442, John Wiley & Sons, Inc., USA.

Park, J., et al., "Evaluation of an Energy-Based Approach and a Critical Plane Approach for Predicting Constant Amplitude Multiaxial Fatigue Life,", International Journal of Fatigue, 2000, pp. 23-39, vol. 22, Elsevier Science Ltd., UK.

\* cited by examiner

IN VITRO TEST METHOD FOR IMPLANT MATERIALS

CROSS REFERENCE TO RELATED APPLICATIONS

This application is a national stage application, filed under 35 U.S.C. §371, of International Application No. PCT/FI2012/050362, filed Apr. 13, 2012, which claims priority to and the benefit of U.S. Application No. 61/475,684, filed Apr. 15, 2011, the contents of all of which are hereby incorporated by reference in their entirety.

BACKGROUND OF THE INVENTION

Related Field

The present invention relates to an improved method for testing materials in vitro. Further it relates to an apparatus for in vitro testing.

Description of Related Art

It is general practise to test biomaterials for implants in two separate ways. Testing of materials is being conducted in two major areas: mechanical testing or characterization of the material itself, i.e. strength, hardness, fatigue, coatings adhesion strength, and biological testing, such as materials biocompatibility, cytotoxicity, bioactivity (e.g. hydroxyapatite growth in vitro), etc. Many biomaterials, including those for implants, are being nowadays tested under different mechanical loading schemes, specified by various standards. Mechanical tests do not usually involve any kind of biological objects. For example, ASTM F2028-02 uses polyurethane as a bone substitute.

Besides conventional (tensile, bending etc.) tests for materials themselves, there are also dedicated test for implant materials such as fatigue tests (e.g. ISO 14801 for dental implants). These tests are targeting on determination of a few parameters only, such as tensile strength, high-cycle fatigue limit, and they are mostly destructive. Their main purpose is to determine the practical limits of materials in service conditions from mechanical point of view only. The most advanced but costly and time-consuming, yet destructive tests are performed at different implant simulators, such as hip simulators, knee simulators, where specific loading patterns are imposed and the wear, fatigue and joint materials degradation is observed. For example, WO 03/009780 discloses the device for fatigue testing of an implantable medical device under compression. For load-bearing implant materials, such as titanium alloys, a typical test is rotating bending fatigue (RBF). WO 2008/022944 discloses fatigue test system for repetitively deforming a tubular implant structure.

Conventional biological tests evaluate biomaterials ability to work in vitro, such as ISO 10993 Parts 3, 5, 9, 12, 14-18. Tests are being carried out in respective culture wells or similar devices with only goal to access the effect of materials (in direct contact or via an extract) on living cells in static conditions. Studies relate to e.g. pharmacological issues (drug elution) and their impact on biological response of the tested material. For example, WO84/03047 discloses an in vitro method for determining the efficacy of therapeutic agents in an artificial capillary or membrane-type cell culturing apparatus. This method is intended for artificial organs (heart, kidney) cytotoxicity analysis.

BRIEF SUMMARY

It is an object of the present invention to provide a method for in vitro testing of biomaterials, such as materials for preferential use in load-bearing implants. It is a further object to provide an apparatus for testing.

Thanks to the present invention, controlled and prescribed mechanical loading of specimen can be linked with determination of biological activity or other similar properties of the material. Thus, it is possible to achieve combination of test results capable to answer, for example, whether the material is good for osteogenesis and whether it is biocompatible at the same time.

According to a first aspect of the invention an in vitro test method for determining the potential capability of a material or a device to perform in in vivo conditions is provided. The test method comprises at least the following steps: immersing at least a part of a test specimen into a liquid media, controlling the liquid media, controlling surrounding environment, providing a predetermined non-destructive force to the specimen, and measuring reactions of the specimen or constituents of the liquid media. Thus, the test method may comprise inducing both mechanical forces (causing stress/strains) and biological/chemical stimuli to the test specimen, complemented with a fluid flow in the vicinity of the material specimen. Further, the biological activity of the material can be determined.

According to a second aspect of the invention an apparatus for in vitro testing of a specimen is provided. The apparatus comprises at least means for immersing at least a part of a test specimen into a liquid media, means for controlling the liquid media, means for controlling surrounding environment, means for providing a predetermined non-destructive force to the specimen, and means for measuring reactions of the specimen or constituents of the liquid media.

Further embodiments are presented in the dependent claims.

The liquid media may comprise at least one of the following: water, saline or buffered solution, simulated body fluid, extracellular matrix liquid, blood or blood substitute, designated cells culture, bacteria culture, virus culture, pharmaceutical or biological compound or any combination thereof.

The controlling the liquid media may comprise adjusting and monitoring at least one of the following parameters: composition, pH, temperature, pressure, or flow velocity of the liquid. In addition, controlling surrounding environment may comprise adjusting and monitoring of the gas atmosphere. Further, the providing of the force may include application of adjusted repetitive elastic deformation. In addition, the liquid media may be controlled and predetermined force may be provided so as to form non-zero mechanoregulation index, which is between 1 and 3 or equal to or less than one.

Measuring the reactions of the specimen may include at least one of the following: analysing of the liquid media; or analysing of the test specimen. Analysing may comprise determination of at least one of the following: drug elution, drug(s) agonism, efficacy, activity, potency, selectivity, or tachyphylaxis or any combinations thereof. It may also comprise at least one of the following: analysing of cytotoxicity, cell proliferation and growth, cell differentiation, gene expression or inflammatory potential, or bacterial or viruses proliferation, growth and attachment or combinations thereof. Analysis may also comprise measuring of biofilm formation or it may comprise a prescribed and externally applied sterilization stimulus.

DESCRIPTION OF VARIOUS VIEWS OF THE FIGURES

Figure 2:
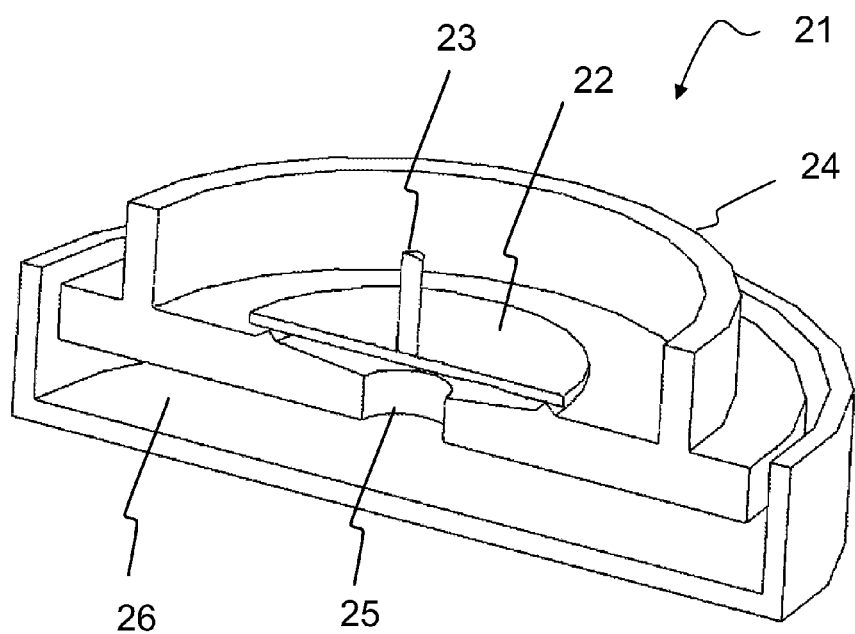

The invention will be explained in the following with reference to the appending drawings, where FIG. 1 presents the principle of the test method, FIG. 2 presents, in cross-sectional view, one example embodiment of the testing apparatus.

DETAILED DESCRIPTION OF VARIOUS EMBODIMENTS

According to the invention a novel test method and apparatus for material characterization is provided. Thanks to the test method a combined materials characterization is accomplished. The test method is also called as an in vitro test, referring to a test performed outside a living body. A testing method comprise an application of controlled and prescribed mechanical loading of specimen, immersed into a liquid media, to create a proper combination of mechanical, fluidic and biological stimuli to determine suitability (biocompatibility) of the material for its intended application in the conditions as close as possible to hostile in vivo. In addition, the method allows simultaneous or separate evaluation of effects of bacterial contamination (biofilm formation), pharmacological factors, sterilization actions, etc. depending on the objectives of the study.

Referring to FIG. 1, in some example embodiments the test method comprises application of mechanical forces F to the test specimen 2. Prior to testing the test specimen is adjusted on top of the fixed support 4. In addition, the test method comprises specified liquid media 6, wherein the specimen is at least partly immersed. Also surrounding environment, such as atmosphere 8 can be controlled. Furthermore, the reactions of the specimen 2 with the liquid media and/or surrounding environment may be measured or monitored. Also some of the constituents of the liquid media may be measured or monitored. None of the measurements used would cause a significant or uncontrolled perturbation of the media properties. For example, the biological activity of the specimen occurring during testing can be measured or monitored (analysed). In other words, the test method allows combining testing of biological activity with mechanical loads (strains) and fluidics normally present at the body conditions, thus corresponding to more realistic situations, i.e. when the material is implanted into a living body (in vivo).

In this application test specimen, specimen or test sample refers to a piece of a material to be tested, such as a biomaterial consisting synthetic, natural or modified natural material intended to be in contact and interact with the biological system. Materials include at least but are not limited to ceramic, metal, polymer, composite and biological materials, such as an organ, a tissue or tissue engineered products. The material may also include additional chemical, biological and/or pharmaceutical substances, which may be integrated, embedded, or placed on the surface of the material as a coating.

Preferably, the testing is used for materials which are intended for use in interaction with body, also called as biomaterials. Especially, the testing method is used for testing of biomaterials to be applied in load-bearing implants or prostheses. Implant refers to a medical device made from one or more biomaterial that is placed into a surgically or naturally formed cavity of the human body. Prosthesis refers to an artificial device made to replace or augment a missing or impaired part of the human body.

The test method is essentially a non-destructive testing (NDT) of the specimen, wherein the properties of a test sample are evaluated without causing irreversible mechanical damage to the specimen. Test may be also called as a non-destructive examination (NDE). Since the method is non-destructive, it gives a possibility for post-examination of the specimen on different levels, for example ex situ analysis of cells, bacteria or biofilms, pharmacological substances by any suitable known method. Additionally, this allows re-use of the same test specimen for the next tests, providing the testing history of the specimen to be recorded and taken into account.

The test method provides enhanced in vitro simulation of biomaterials, i.e. more efficient evaluation of a material in the conditions close to a hostile environment (in vivo). For example, the test may be carried out under prescribed repetitive deformation, controlled microfluidic velocity field and milieu parameters including biological substances and species etc. By providing more efficient evaluation method for the materials and implants there may be, for example, a substantial decrease of the risk of biomaterial related infections (BRI) of implants e.g. orthopaedic and dental implants, reduced risks of hypersensitivity, foreign body neoplasms and osteolysis. Biomaterial related infections generally originate from bacterial contamination during surgery by exogenous sources, such as patient's skin or external sources in the environment. In addition, the amount of in vivo tests or clinical tests required may be reduced. Also optimization of materials and implant's designs satisfying biomechanical and biomedical requirements may be achieved. Thanks to the test method including both proper microfluidics (liquid media) and microstrains (e.g. shear strain), it is possible to mimic host conditions at the bone/biomaterial interface and to measure e.g. the material capability to osteointegration.

According to an embodiment, the method provides a combined material characterization, i.e. simultaneous measurement of various material characteristics, such as the biocompatibility of the materials and other biological activities. Biological activity refers here cell proliferation and growth, cell differentiation, gene expressions, inflammatory potential, osteointegration, cytotoxicity, genotoxicity, and in selected cases also potential carcinogenicity, hemocompatibility, drug elution or release, or other properties disclosed e.g. in the standard ISO 10993. As an example, there is an ability to provide an answer whether the material is good for osteointegration and whether it is biocompatible at the same time. Osteointegration potential may be evaluated, for example, by measuring the simultaneous formation of calcium phosphate precipitates, osteogenetic cells adhesion, proliferation and gene expression.

Measurements of material characteristics, such as reactions of the specimen with the liquid media and/or with the surrounding environment (gaseous atmosphere), may include analysing of the liquid media and/or analysing of the test specimen either in situ during the test procedure or after the experiment (testing procedure). The analysis may comprise determination of: drug elution, drug(s) agonism, efficacy, activity, potency, selectivity, or tachyphylaxis, or any combinations thereof, relevant to the intended specific drug purpose. Alternatively, analysis may comprise evaluation of cytotoxicity, cell proliferation and growth, cell differentiation, gene expression or inflammatory potential, or bacterial or viruses proliferation, growth and attachment or any relevant combination of the parameters of interest. Analysis may also comprise measuring of biofilm formation, using bacterial cultures with or without additional components, cultures and/or additions.

Biocompatibility refers here to the ability of a material to perform with an appropriate host response in a specific application, i.e. not having toxic or injurious effects on biological systems. Biocompatibility analysis include e.g. in vitro cytotoxicity testing of materials, in vitro characterization of human cell/coating interactions, cell attachment and proliferation, cells differentiation (molecular biology), inflammatory potential (monocyte-macrophage, interleukin levels), etc. Osteointegration potential refers here to the ability of the material or implant to provide direct structural and functional linkage with bone tissue by formation of new bone or bone-like structure in the vicinity of the material/tissue interface. Osteogenesis refers here to the process of new bone formation and growth. It may also assume respective formation of other tissues such as fibrous or cartilage.

According to some example embodiments of the invention, test parameters can be modified in order to simulate different in vivo environments. Further, the test parameters may be dependent on the material being tested and the study objectives. According to an embodiment of the test method, it includes parameters, such as external mechanical stimulus (motions and force) and fluidic stimulus (liquid media).

The mechanical stimulus may comprise bending, torsion, shear, rotation or any combination thereof, depending on the material application purpose. The mechanical stimulus has a predetermined intensity, amplitude, frequency and duration.

According to some example embodiments, mechanical stimulus comprises providing a predetermined non-destructive force to the specimen in order to apply an adjusted repetitive elastic deformation with the goal of creation of a prescribed repetitive strain in the test specimen close to strain levels observed or expected to appear in the host in vivo conditions, relevant for the selected implant or material being evaluated. Thus, the mechanical stimulus may mimic both microstrains and the micromotions of the test specimen, similar to those occurring when the material is being implanted in a human body. For example, for THR (total hip replacement) implants the loading cycle is commonly about of 0.5-1 Hz with a special wave pattern. In addition to the oscillating load, micromotion of the implant is controlled.

According to some example embodiments of the invention, when the specimen is immersed into a liquid media, the test method further comprises a controlled microfluidic velocity during the specimen oscillate movement accompanied, if necessary, by varying media parameters such as pH, temperature, species concentration, addition of biological substances and/or living cultures. Test method may also comprise in situ sterilization, e.g. chemical, radiative (gamma-rays) or electromagnetic (ultraviolet, intensive blue), either during or between the measurements.

As an example, applied testing parameters may be described by the mechanoregulation index M:

$$M = \frac{|U|}{3} + \frac{\varepsilon_{res}}{0.0375},$$

where |U| is the average liquid flow velocity magnitude in the vicinity of a surface of the test specimen (or inside the pores of the specimen) in μm/s and $\varepsilon_{res}$ is the resolved average octahedral strain magnitude:

$$\varepsilon_{res} = \frac{2}{3}\sqrt{(\varepsilon_1 - \varepsilon_2)^2 + (\varepsilon_2 - \varepsilon_3)^2 + (\varepsilon_1 - \varepsilon_3)^2},$$

where $\varepsilon$ are principal strains for main coordinates axes 1, 2 and 3. When index M>3, fibrous tissue preferably forms; when 1<M<3, cartilage preferably forms. M values below unity leads to preferential formation of the bone (van C. Mow, R. Huiskes, Basic orthopaedic biomechanics and mechano-biology, $3^{rd}$ ed., Lippincott Williams & Wilkins, 2005, 720 pp.). For different biomaterials applications, another form of the M index may also be used. The above equations are considered here as one possible example.

Tests may be performed under different loads and frequencies, within the limits of the equipment and sample holder design type. As an example, for osteointegration the mechanoregulation index (M) should be less than unity. Thus, when bone formation is relevant for implant, the testing parameters are adjusted in such a way that M<1 for the acceptable load limits (load is selected according to the specimen thickness and elastic properties to cause proper strain $\varepsilon_{res}$). However, if the cartilage or fibrous tissue formation is of an interest, M index could be made larger by adjusting the testing parameters.

Thanks to the test method according to an example embodiment of the invention, e.g. controllable and adjustable microfluidic flow and micromotions inside the porous test specimen can be provided. Thus, more realistic test results correlating with realistic implant conditions may be achieved. In addition, studies relating to e.g. drug release or elution and its impact on biological response of the tested material may be connected to mechanical stimulus and fluid flow.

In the test method comprising mechano-fluidic stimulus (comprising both mechanical and fluidic stimulus), the fluid, also called as a liquid media, may include, for example, water, saline or buffered solutions, simulated body fluids, extracellular matrix liquid, blood or blood substitute, designated cells, bacteria and/or viruses cultures, pharmaceutical and/or biological compounds (such as but not limited to drugs, carriers, serum, factors, proteins, DNA, RNA, enzymes, etc). Cells may include, for example, human osteogenic cells or human endothelial cells.

According to an embodiment, the liquid media constitution allows creation of any relevant combination of acting stimuli to evaluate required biomaterials performance in question. For example, application of simulating body fluid (SBF) alone allows studying precipitation and growth of calcium phosphates and carbonates on the surface of the material. Addition of human osteogenic cells to the media would allow evaluation of the cell presence effect on bone-like formation. If bacteria are also injected in the media, competitive effects of cells and bacteria adhesion and proliferation might be evaluated at the same time. Such studies might be composed of any reasonable complexity.

According to the present invention, the environment conditions, such as surrounding atmosphere, of the test process are also controllable. For example, temperature may be at around 37.0±0.5° C., gas pressure at around 101.3 kPa and gas composition may be air including 5% $CO_2$. In some cases, pH of the liquid media may be constant (buffered solution) whereas in other cases liquid flow rate might be fixed (to control the liquid refreshment rate). The combination of these parameters is selected on the case basis depending on the tests objectives.

Within the present invention, the oscillating mechanical force is being applied to the specimen in order to create adjusted repetitive elastic deformation (i.e. without irreversible deformation of the specimen). This strain tensor in the specimen should be close to the strain levels observed or expected to appear in the host in vivo conditions, relevant for the selected implant or material being evaluated. For instance, 0.1-30 millistrains (strains×0.001) is the typical range for bone formation in orthopaedic applications (van C.

Mow, R. Huiskes, Basic orthopaedic biomechanics and mechano-biology, 3$^{rd}$ ed., Lippincott Williams & Wilkins, 2005, 720 pp.).

It is also important that in addition to purely mechanical strain, fluid velocity in the vicinity of the specimen is important factor for osteogenesis, growth of cartilage or fibrous tissue. It also affects biofilm formation by bacterial interactions, as the fluid flow plays an enormous role in all biological systems metabolism and proliferation. Thus, a combination of the fluid flow and mechanical deformation is an important feature of the test method of the present invention.

According to an embodiment, the test method may be used for measuring drug elution, drug(s) agonism, efficacy, activity, potency, selectivity, tachyphylaxis, etc., when the drug is located either on the surface of a coated or uncoated implant or deliberately added to the media surrounding the specimen.

The drug elution or release analysis may be performed on-line from the liquid media for instance aliquot off-samples necessity could be eventually eliminated with see-through spectrometry (IR, UV, Raman or the like), where specific molecular groups are monitored. This analysis might be more accurate and sensitive to minor oscillations of the drug activity or cell population control. However, the analysis does not exclude existing methods as fluorescent microscopy, which can be applied after the test, and such analytical techniques are not in the scope of the present invention.

In many cases, presence of living media, its metabolism and activity cover the real kinetics of drug elution and activity. Therefore, it is also possible to measure pure physical-chemical effects (such as drug elution form porous coatings or substrates under applied oscillating mechanical loads but without living media) but also pharmacological effects as mentioned. Exact testing procedure will depend on the drug used and characteristics required.

According to an embodiment of the invention, the test method further comprises an additional chemical stimulus, such as pH variation via external titration. Single/periodic sterilization may also be applied such as gamma-rays, UV or intensive blue light (405 nm). This may mimic the behaviour of the implant specimen under more extreme conditions such as wounds where pH may strongly deviate from the nominal value or when the implant surface is subjected to an external sterilization. The latter may also be applied in the sense of cleaning the system between measurements without needs of extra autoclave or ethylene oxide sterilization steps.

According to an embodiment, the test method may be used for implant materials for simultaneous measurement of their biomechanical properties, biocompatibility, bioactivity, cytotoxicity at conditions closest to realistic applications. In addition, the pharmacological activity of the implant materials in the presence of external controlled sterilization stimulus may be measured, as mentioned above. Further, in vitro cells proliferation and growth, differentiation, gene expressions, inflammatory potential and other parameters may be measured, e.g. by a cell counting using external light diffraction, flow cytometry or correlation spectroscopy methods.

Also, more complicated tests and analysis comprising deliberate biofilm formation, effect of sterilization, etc. simultaneous measurements, may be obtained. Biofilm refers to a complex aggregation of micro-organisms growing on a solid substrate, such as the surface of a biomaterial or an implant. Biofilm formation is generally the major pathogenic factor in the foreign body associated infections of the implants, which may further cause failure of the implant. Biofilm formation may be measured, for example, using bacterial or virus proliferation, growth and attachment or any relevant combination of the parameters of interest.

In the present invention it is not only possible to combine different inorganic and organic components, but also deliberately carry out tests with "ideal" living environment in vitro or in the "contaminated" non-sterile media to which specific bacteria and other micro-organisms or viruses have been added (e.g. S. aureus, E. coli) to evaluate parameters like cell adhesion, proliferation and growth under the proper mechanical stimulus instead of static soaking of a specimen in a culture well. The mechanical stimulus imposed on the test specimen is similar to that existing in the living body.

The method may also be applied to study biofouling process in chemistry, environment and other applications, where test specimen is not an implantable material, but a part of a device being subjected to biological, mechanical and fluidic factors (catheters, in vitro devices, analytical devices such as bio-MEMS, apparatus, pipelines, and numbers of others).

According to some embodiments of the invention, an apparatus for in vitro testing of a test specimen comprises means for immersing at least a part of a test specimen into a liquid media, means for controlling the liquid media, means for controlling the surrounding environment, such as gas atmosphere; means for providing a predetermined non-destructive force to the specimen, and external means for measuring reactions of the specimen or constituents of the liquid media. Referring to FIG. 2, the apparatus 21 comprises at least one sample holder 24 having at least one orifice 25, a punch 23 and a bath 26 in order to allow the immersion of the specimen 22 at least partially in the liquid media, to control a movement of the specimen, to adjust a predetermined non-destructive force, such as cause a proper elastic deformation with prescribed amplitude, phase, frequency and duration ranges via the punch 23 to the specimen, and to provide respective fluid flow to/from the specimen via an orifice 25. Thus, the punch 23 is for application of force (causing stress/strains) to the specimen and the orifice 25 is for controlling the liquid flow to or from the specimen chamber.

The embodiments described above are only example embodiments of the invention and a person skilled in the art recognizes readily that they may be combined in various ways to generate further embodiments without deviating from the basic underlying invention.

The invention claimed is:

1. A non-destructive in vitro testing method of a specimen, the method comprising the steps of:
    immersing at least a part of the specimen into a specimen chamber containing a liquid media;
    controlling surrounding environment, said surrounding environment comprising gaseous atmosphere;
    imposing, via a punch, a predetermined non-destructive force providing adjusted repetitive non-destructive elastic deformation upon the specimen;
    controlling the liquid media in the vicinity of the specimen by controlling, via an orifice of said specimen chamber, a flow velocity of the liquid media, the flow velocity having been generated in the liquid media by the predetermined non-destructive force imposed via the punch, wherein said orifice is configured to control the flow velocity of the liquid media at least one of to or from the specimen chamber; and
    measuring in situ reactions of at least one of the specimen or constituents of the liquid media, said reactions being generated by the imposition of the predetermined non-destructive force and by the flow velocity of the liquid media generated in the specimen chamber by the predetermined non-destructive force.

2. The method according to claim 1, further comprising adjusting and monitoring at least one of the following parameters: composition, pH, temperature, pressure, or flow velocity of the liquid.

3. The method according to claim 1, wherein controlling surrounding environment comprises adjusting and monitoring of the gas atmosphere.

4. The method according to claim 1, wherein the liquid media is controlled and the predetermined non-destructive force is provided so as to form a non-zero mechanoregulation index, wherein the index is between 1 and 3.

5. The method according to claim 1, wherein the liquid media is controlled and the predetermined non-destructive force is provided so as to form a non-zero mechanoregulation index, wherein the index is equal to one.

6. The method according to claim 1, wherein the liquid media is controlled and the predetermined non-destructive force is provided so as to form a non-zero mechanoregulation index, wherein the index is less than one.

7. The method according to claim 1, wherein the step of measuring the reactions of the specimen comprises at least one of the following: analyzing of the liquid media; or analyzing of the test specimen.

8. The method according to claim 7, wherein the step of analyzing of at least one of the liquid media or the specimen comprises a determination of at least one of the following: drug elution, drug(s) agonism, efficacy, activity, potency, selectivity, tachyphylaxis, or any combinations thereof.

9. The method according to claim 7, wherein the analyzing of at least one of the liquid media or the specimen comprises at least one of the following: analyzing of cytotoxicity, cell proliferation and growth, cell differentiation, gene expression or inflammatory potential, bacterial proliferation, viral proliferation, growth and attachment, or combinations thereof.

10. The method according to claim 7, wherein the step of analyzing comprises measuring of biofilm formation.

11. The test method according to claim 7, wherein the step of analyzing comprises a prescribed and externally applied sterilization stimulus.

* * * * *